Feb. 2, 1965 H. M. TIRET Plant Pat. 2,468
FUCHSIA PLANT
Filed Nov. 12, 1963
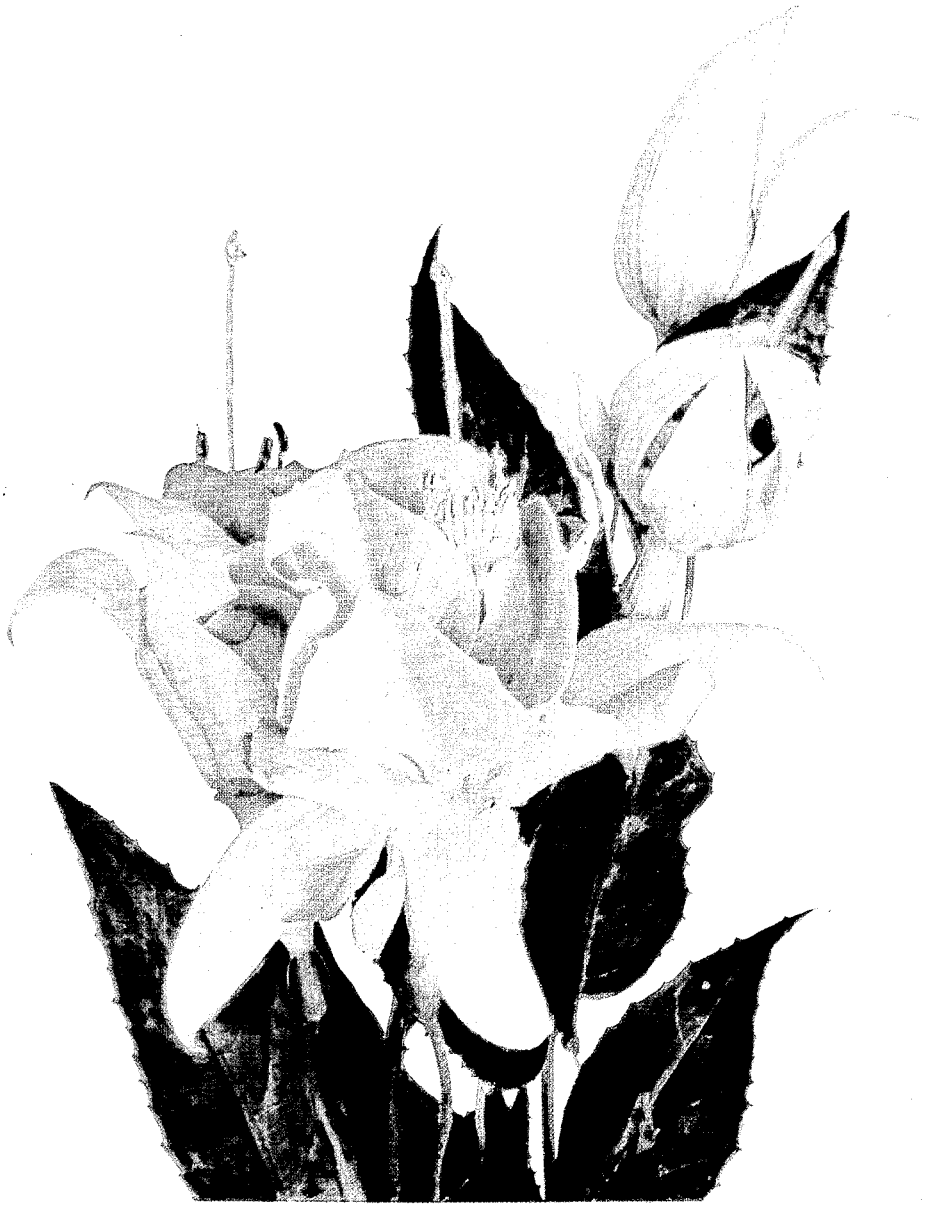

United States Patent Office

Plant Pat. 2,468
Patented Feb. 2, 1965

2,468
FUCHSIA PLANT

Horace M. Tiret, 2126 Taraval St., San Francisco, Calif.

Filed Nov. 12, 1963, Ser. No. 323,186
1 Claim. (Cl. Plt.—84)

This invention relates to a new and improved fuchsia plant, the principal new and different characteristic of which is the delicate pastel color of the flower combined with unusual form and superior trailing habit of growth.

As a hybrid from a seedling (unpatented) not introduced to the trade, namely 12–89–15 and unknown seedling (unpatented), the figure representing applicant's own breeding symbols, the plant has been asexually reproduced at Colma, California, by cuttings which retained the characteristics of the parent fuchsia.

The plant is a natural trailer and grows vigorously. It is very self-branching with large delicate pastel flowers. The flowers are produced in abundance. It is an early bloomer.

In the accompanying drawing, the figure shows a typical branch tip; the drawing representing approximate actual size.

A detailed description of this new variety of fuchsia plant follows:

*Habit of growth.*—Vigorous, trailing variety. Blooms early.

*Foliage.*—Small in size, dark green in color. Leaves are veined with edges heavily serrated. Branches are reddish-brown. The mature leaf is approximately 2¾″ in length and 1½″ in width at the widest point.

*Petals.*—The petals are mauve (British Horticultural Chart #633/1 and #633/2). There is a slight variation between #633/1 and #633/2.

The petals number 27 (approximately). The corolla is gracefully loose in form. Outer petals flare out from center petals. The diameter of the mature flower is approximately 2¾″. Length of the large petals is 1¾″, width 1¾″ (spread out). Appearance of the petals is smooth.

*Ovary.*—Bright green in color. Length ½″, width at widest point 5/16″, when flower is fully open.

*Tube.*—Long and slender. Length approximately 1″, width at widest point ¼″. Color is pale carmine rose.

*Sepals.*—Topside is carmine rose with ivory tip (British Horticultural Chart #621/1). Underside is carmine rose #621/2. Sepals are slender in form, and curl back against tube. They are four in number, 1¾″ in length and ⅝″ in width at widest point. Outer side; smooth and satiny, underside; crepelike in appearance.

*Stamens.*—Eight in number, flesh colored with pale pink anthers. Slender, length 2¼″.

*Pistil.*—The style is approximately 3″ in length and ⅛″ in width. It is flesh color, while the stigma is pale rose.

*Buds.*—Pale carmine rose with green tips that fade into ivory as flower matures. Length from ovary is approximately 3″, and width at widest point is 1″.

*Parentage.*—Applicant's own seedlings (unpatented). Not introduced to the trade. Applicant's breeding symbol 12–89–15 (unpatented) and unknown seedling (unpatented).

Having thus disclosed my discovery, I claim:

A new and distinct variety of fuchsia plant herein described, characterized by the delicate pastel color of the flower combined with unusual form and superior trailing habit of growth, resulting in an appearance unlike any fuchsia of its type.

No references cited.

ABRAHAM G. STONE, *Primary Examiner.*